(12) United States Patent
Hill

(10) Patent No.: US 6,907,292 B1
(45) Date of Patent: Jun. 14, 2005

(54) DEVICE IN CONNECTION WITH PACERS

(75) Inventor: Rolf Hill, Järfälla (SE)

(73) Assignee: St. Jude Medical AB (SE)

( * ) Notice: Subject to any disclaimer, the term of this patent is extended or adjusted under 35 U.S.C. 154(b) by 0 days.

(21) Appl. No.: 09/856,888

(22) PCT Filed: Nov. 15, 1999

(86) PCT No.: PCT/SE99/02083
§ 371 (c)(1),
(2), (4) Date: Feb. 5, 2002

(87) PCT Pub. No.: WO00/32268

PCT Pub. Date: Jun. 8, 2000

(30) Foreign Application Priority Data

Nov. 30, 1998 (SE) .............................. 9804138

(51) Int. Cl.$^7$ ............................................. A61N 1/375
(52) U.S. Cl. .......................... 607/37; 439/909; 439/288
(58) Field of Search ..................... 607/36, 37; 439/153, 439/160, 261, 288, 295, 341, 816, 823, 864, 909

(56) References Cited

U.S. PATENT DOCUMENTS 4,347,849 A  9/1982  Congdon
4,784,141 A  11/1988 Peers-Travarton
5,252,090 A  10/1993 Giurtino et al.
5,489,225 A  2/1996  Julian

FOREIGN PATENT DOCUMENTS

EP  0 786 269  7/1997

Primary Examiner—Jeffrey R. Jastrzab
(74) Attorney, Agent, or Firm—Schiff Hardin LLP

(57) ABSTRACT

The invention relates to a locking device (1) for a female connector part for cooperation with an elongate, male connector part (30), said female connector part being intended for use in a pacer housing. Said female connector part comprises a longitudinal bore defining a longitudinal space for said locking device. Said locking device comprises one or several tongues (19, 19') being swingable between two positions, a first position in which the tips of the tongues (19, 19') can engage said male elongate connector part (30) and a second position in which the tips of the tongues (19, 19') will not engage the male elongate connector part (30). Said tongues are biased towards said first position by means of a spring force. A pivot (9) is associated with each tongue and each tongue has a first part engaging said connector means (30) and being located on one side of said pivot and a second part being located on the other side of said pivot. Longitudinally acting means (4) are provided to act on said second part of said tongues (19, 19') for actuating said tongues from said first position against said bias to said second position.

10 Claims, 3 Drawing Sheets

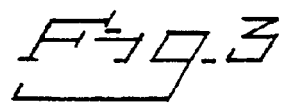
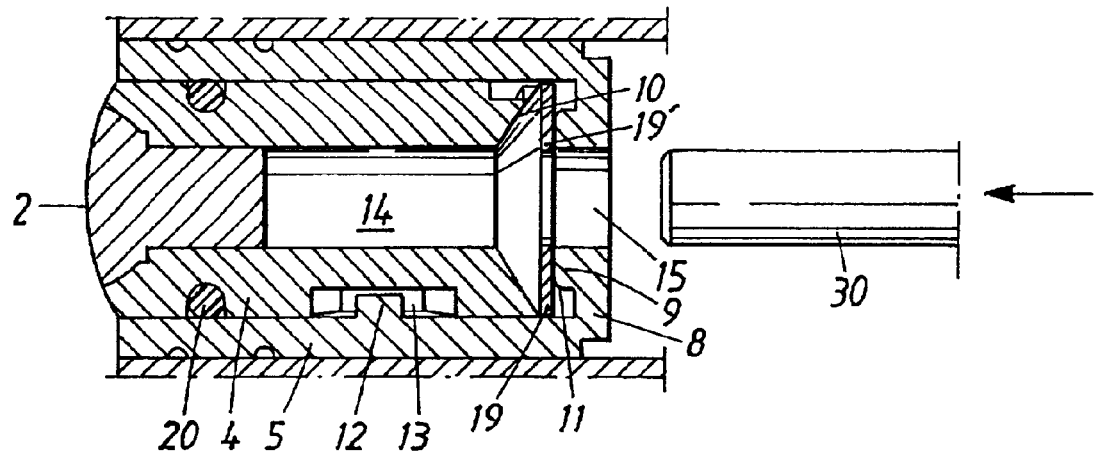
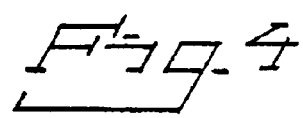
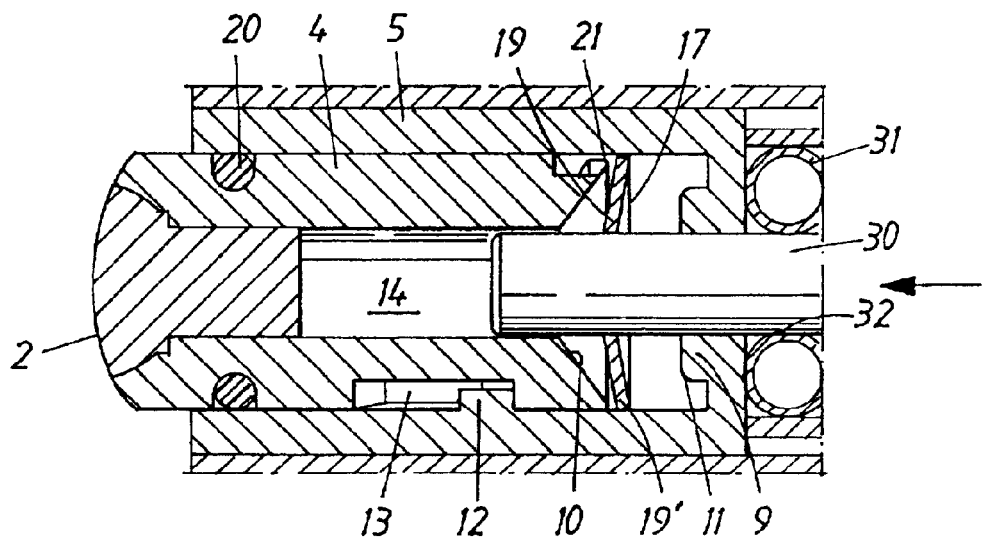

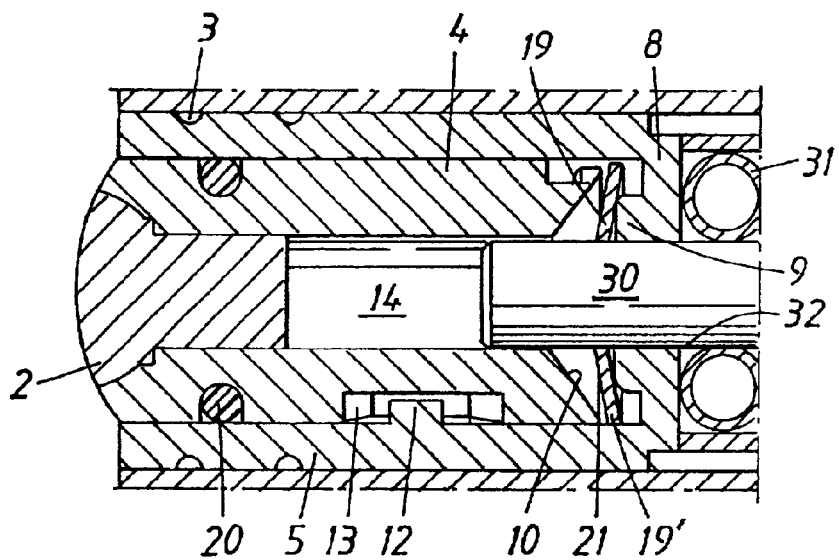
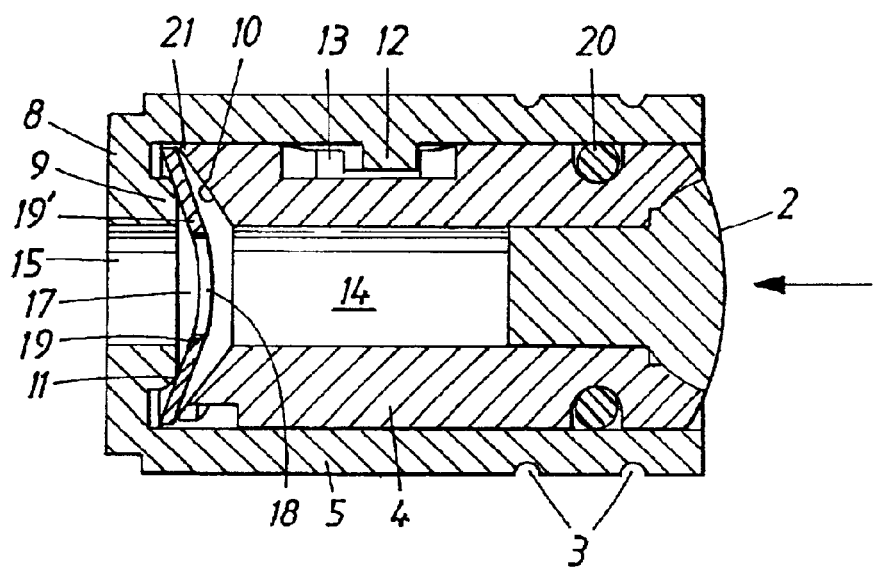

DEVICE IN CONNECTION WITH PACERS

BACKGROUND OF THE INVENTION

1. Field of the Invention

The present invention relates to a connector for connecting leads to a housing for an implantable pacer.

2. Description of the Prior Art

A pacer system normally comprises a pulse generator located in a pacer housing, leads and electrodes at the distal end of the leads. The proximal end of the leads is connected to the pacer housing by means of a releasable connector. The connector comprises a female connector part in the pacer housing. The proximal end of the lead normally is designed as a standardized male connector part and the female connector part normally is standardized to such an extent that it will receive this standardized male connector part. The most common way of fixing or locking the male connector part in the female connector part is to use set screws which are oriented in an orthogonal direction in relation to the male connector part and which are accessible from the outside of the pacer housing. The female connector part normally is located in a header molded on to the housing.

While these setscrews generally have a good fixing effect, the screws are somewhat difficult to handle, the screws being small. For this reason, attempts have been made to develop fixing means, which more or less automatically lock the male connector part upon insertion thereof.

One such device is for instance disclosed in U.S. Pat. No. 5,252,090. This device includes two elastically resilient metal tongues in a female connector part. The tongues are situated in a common plane and have a common central line, with a respective free end, which are located oppositely to each other. The distance between the two free ends is smaller than the diameter of the male connector part. The tongues will be deflected into the direction of insertion when the male connector part is inserted into the female connector part and the tongues thus will engage and lock the sides of the male connector part. If the male connector part is pulled outwardly from the female connector part, the locking effect will increase. The reason is that the friction between the tongues and the male connector part will draw the tongues in closer contact with the male connector part. The two tongues are integrally connected to two wings extending through openings in the header. The wings are angled in relation to the plan of the tongues. Pressure on the wings will move the tongues out of engagement with the male connector part, which then can be removed.

In similarity with the design using setscrews, the locking means in the above design have to be accessed laterally from the outside. For this reason, the locking means are located in the header in order to avoid openings for manipulation in the parts of the housing in which the electronic parts of the pacer are located. Any openings for the connections in the housing or can into the interior of the housing from the header can be permanently sealed.

Another design of a device for locking the terminal pin of a male connector plug is disclosed in U.S. Pat. No. 4,784,141. This device is designed for location in one open end of a bore through a header or through the pacer and is accessible from that end. The male plug is to be inserted through the opposite end of the bore. The locking device comprises a hollow cylindrical part with interior threads and an interior, end flange with a conical interior surface. The locking device further comprises a plug with a central bore and with external threads fitting the interior threads in the cylindrical part. The inner open end of the plug is also provided with a conical surface. A resilient locking ring with conically shaped sides is located between the respective conical surface on the plug and on the cylindrical part. When the plug is screwed inwardly into the cylindrical part, the conical surfaces on plug and cylindrical part will compress the locking ring inwardly against a connector pin inserted into the locking part. In this way the pin is locked in the locking device.

SUMMARY OF THE INVENTION

The primary object of the invention is to provide a connector locking part of the kind described above, which can be used with standard male connector parts, which involves a positive locking effect and which does not need any lateral openings in the connector housing or the pacemaker housing. At the same time, it should be possible to easily remove the male connector part without any need of manual operations involving special tools. The object further is to provide a connector that is suitable for use in so called black holes. Black holes are connectors made directly in the pacer housing without any need for the commonly used molded-on connector parts in the form of headers. A further object is to provide a connector that will indicate visually when the male connector plug has been inserted correctly.

DESCRIPTION OF THE DRAWINGS

FIG. 3 illustrates the locking device just before the insertion of a male connector pin.

FIG. 4 illustrates a first locking state indicating a correct engagement.

FIG. 5 illustrates a second locking state.

FIG. 6 illustrates the opening of the locking device.

DESCRIPTION OF THE PREFERRED EMBODIMENTS

In the description below, "longitudinal" relates to the longitudinal direction of the female connector part and "outer end" relates to the end of the locking device accessible from the outside. It should be noted that all reference signs are not repeated throughout all drawings.

Figure 1:
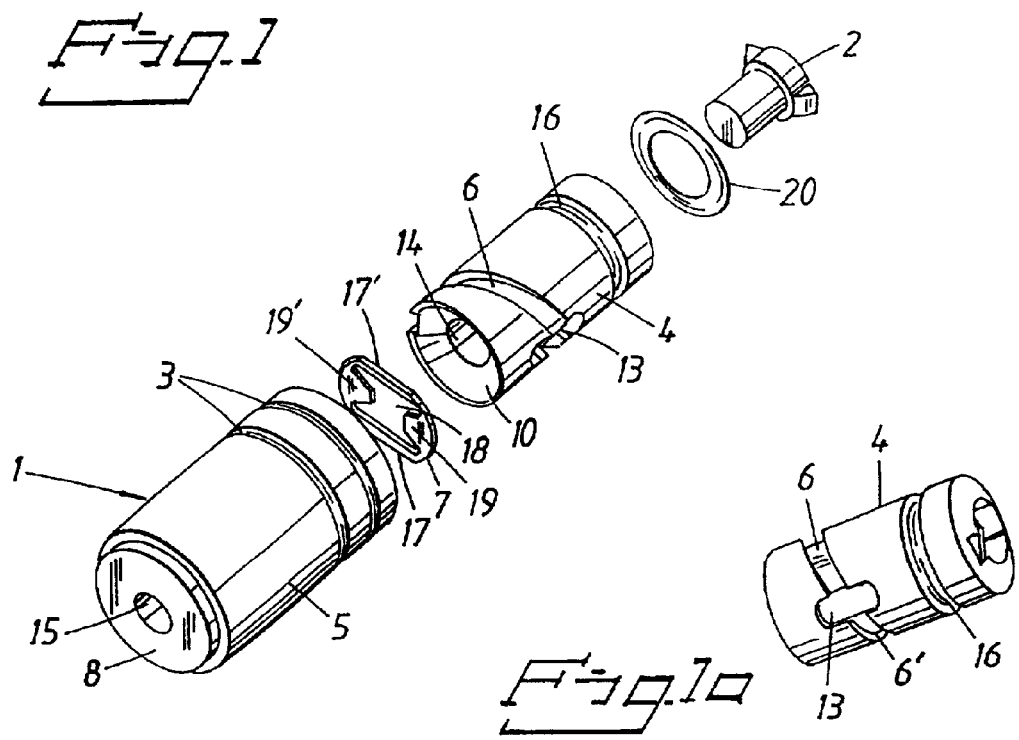
FIGS. 1–1a illustrate the component parts of a locking device for a female connector part in accordance with the invention.

The component parts of a locking part 1 for a female connector according to a preferred embodiment are shown in an exploded view in FIG. 1. The locking part comprises a hollow cylindrical part 5 with an end wall 8 in which a central opening 15 is located. The opening 15 is dimensioned to receive the contact pin of a standard male connector. The outside of the cylindrical part is provided with circumferential grooves 3 serving as space for excess glue when the cylindrical part is glued into a female connector part.

The locking device further comprises a locking washer 7 with a central opening 18. Two locking tongues 19, 19' are located on opposite sides of the opening 18 and extend into the opening. The distance between the tips is less than the diameter of the male connector pin to be locked into the locking device. The washer 7 has an outer shape that includes two parallel sides 17, 17'. The two parallel sides will bias the tongues towards the common plane of the washer. It should be noted that in this particular embodiment the sides have been designed to be parallel in order to define the bending force of the sides of the washer. The design may also be used for locking the washer against rotation, as will be described in connection with an alternative embodiment.

The inside of the inner end wall is provided with a flange 9 around the opening 15. The flange has been placed in such a way that there will be a distance between the flange and the inner surface of the wall of the cylindrical part 5. The edge 11 of the flange facing the inside wall of the cylindrical part 5 is rounded. The flange 9 will serve as a pivot for the tongues.

Figure 1A:
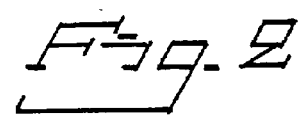
Figure 2:
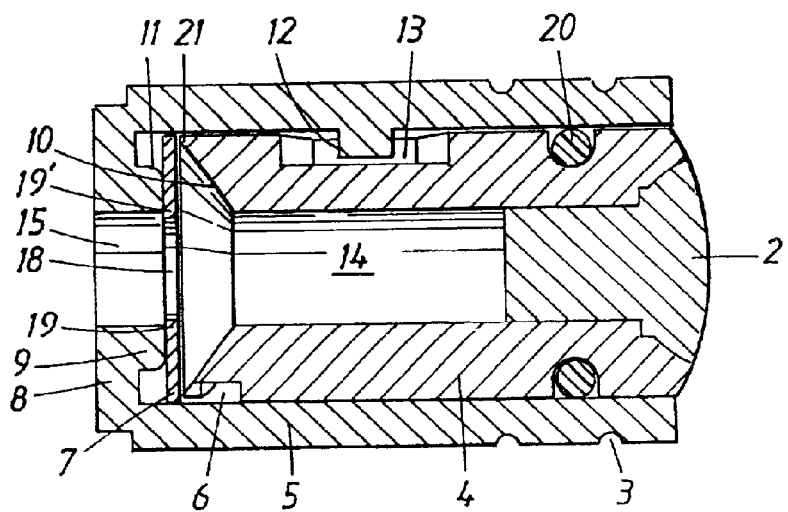
FIG. 2 shows the component parts in FIG. 1 in an assembled state in a section.

The locking device further comprises a cylindrical plunger 4 fitting into the cylindrical part 5. The plunger is provided with a central bore 14 and the outside of the plunger is provided with a spiraling groove 6 intersecting a longitudinal groove 13. These grooves are intended to cooperate with an interior lug 12 located on the inside wall of the cylindrical part 5. The outer side of the outer end of the plunger 4 is provided with a peripheral groove 16 intended to sealingly hold an O-ring 20 against the inside of the cylindrical part 5. As seen in FIG. 1a, a part 6' of the spiraling groove 6 passes beyond the intersection with the groove 13.

The inside of the inner end of the plunger 4 is provided with a conical surface 10, the wall of the plunger 4 thus tapering into a peripheral edge 21.

The outer end of the longitudinal bore of the plunger 4 is closed by means of a plug 2. The opening in the bore is enlarged by means of a slit permitting the insertion of a screwdriver or an equivalent tool.

In the assembled state, illustrated in FIGS. 2–6, the plunger 4 will keep the washer 7 in the vicinity of the flange 9. The plunger will be held in the cylindrical part 5 by means of the longitudinal slot 13, which permits a limited longitudinal movement.

The locking device is simple to assemble. The procedure only comprises the steps of:
placing the washer 7 in the cylindrical part 5,
mounting the sealing ring 20 in the groove 16 on the plunger 4,
engaging the lug 12 in the slot 6 and turning the plunger until the lug 12 is located in the longitudinal slot 13.

The locking device 1 can be glued, welded or otherwise bonded into a tubular connector. The device of course also can be molded into a header.

A male connector pin 30 to be locked into the locking device 1 is inserted through the opening 15 in the end wall 8 as illustrated in FIG. 3. As seen in FIG. 4, the plunger 4 in this particular embodiment can move outwards together with the washer 7 when the pin 30 engages the washer 7. The outward movement is limited by the lug 12 engaging the inner end of the slot 13. In the case in which the locking device is located in a through hole flush with the outer surface of the pacer in which it is to be mounted, the outward movement will be an indication that the male connector pin 30 has been correctly inserted, see FIG. 4.

Since the distance between the tips of the two tongues 19, 19' is less than the diameter of the pin 30, the tongues will be bent in the direction of insertion and consequently form an angle with the surface of the pin. The spring bias of the two parallel sides of the washer will urge the tongues into contact with the pin. The length and the stiffness of the tongues is such that the tongues in principle cannot swing past the plane of the washer, the pin therefore will be locked behind the end wall 8 against withdrawal from the connector.

When the pin has been fully inserted, the plunger 4 can be pushed back into the cylindrical part 5 so as to be flush with the outside of the housing as indicated in FIG. 5.

If the pin is to be disconnected, the plunger 4 is pushed inwardly, the inner peripheral edge 21 engaging the peripheral ends of the washer 7 as illustrated in FIG. 6. As a consequence, the tongues 19, 19' will swing around the flange and release the pin. The pin with lead then easily can be withdrawn.

The removal of the male pin 30 from the connector can be facilitated by removing the plug 2 from the plunger and screwing the plunger into the cylindrical part 5 by means of the groove 6'. The plunger 4 thus will deflect the tongues 19, 19' from the pin. The pitch of the groove is chosen such that the plunger 4 will remain in the rotational position of the screwed-in state in spite of the outward force exerted by the deformed washer 7. The pin then can be pushed out from the connector by means of a suitable tool that can be inserted through the opening of the bore 14.

It should be noted that, in the above embodiment, the washer is not locked against rotation. If however the washer is locked against rotation, it will be possible to locate the tongues (excluding the remaining parts of the washer) on a stud each instead on a circular flange. The studs also will serve s pivots for the tongues. In this case the force needed to swing the tongues out of engagements with the pin would be less, given that the dimensions of the washer remains the same (the spring bias of the tongues into engagement with the pin would however not be affected). In this embodiment the studs are located opposite each other adjacent the central opening 15. The inner side of the wall of the cylindrical part adjacent the studs is shaped to conform to the outer peripheral shape of the washer 7, thus also having two parallel sides in cross-section. The parallel sides are parallel to a centerline drawn through the two studs. In this way, the washer will be locked against rotation when the washer is located on the studs.

In this particular embodiment the inner part of the outside of the plunger would have to have a shape corresponding to the inner shape of the cylindrical part 5. Although the plunger still could be mounted in the cylindrical part by means of a spiraling groove, the option of opening the locking device by rotating the plunger discussed in connection with the above embodiment would be excluded. If this option also were desirable, the means for locking the washer against rotation would have to be located within the outer periphery of the washer and extend past the washer. The inside of the plunger would have to be hollowed to accommodate these means in order to allow the free rotation of the plunger to its innermost location.

The electrical connections from the female connector to the pulse generator are not a part of the present invention and thus are not shown in detail. The connections may for instance be made through circular springs 31 engaging the contact surfaces 32 on the male connector 30, as for instance indicated in FIG. 5. These rings are in turn connected to the interior of the pacer.

The cylindrical part 5 and the plunger 4 may be made of any suitable biocompatible material used in pacers, as for instance metals such s titanium, stainless steel, NP-35 alloy, or ceramics such as Al2O3 or of plastics such as macrolon, epoxy resin etc. The two parts may be made of the same material or of different materials. The tongues and washer preferably is made of titanium, stainless steel or NP-35, but other biocompatible materials having a comparable resilience may of course be used.

The invention of course can be varied in many ways within the scope of the appended claims. In the above embodiments, the washer has been described as having two tongues. It is however quite possible to use only one tongue or more than two tongues. The tongues have been illustrated as being part of a resilient washer, but they may of course be associated with separate springs for instance formed integrally with said tongues. The cylindrical part has been illustrated as a separate part, but may of course be an integral part of a pacer housing or header. In the widest sense, the plunger may be any device transferring a pushing force for the exterior of the pacer to the peripheral parts of the washer.

The male connector part has been illustrated above as being a standard IS-1 male connector with a complementary female connector. The male connector part of course could be of any kind having an elongate shape, the female connector part having a corresponding complementary shape.

Although modifications and changes may be suggested by those skilled in the art, it is the invention of the inventor to embody within the patent warranted heron all changes and modifications as reasonably and properly come within the scope of his contribution to the art.

What is claimed is:

1. An electrical connector arrangement for an implantable medical device, said arrangement comprising:

a female connector part having a longitudinal bore therein adapted to receive a male connector part entering said bore in a first longitudinal direction;

a locking plate disposed in said bore having an opening therein and having at least one tongue formed in said plate projecting into said opening;

a pivot element disposed in said bore;

a longitudinally displaceable element disposed in said bore, said locking plate being disposed in said bore between said pivot element and said longitudinally displaceable element; and said at least one tongue of said locking plate being spring biased to a first position adapted to engage and lock said male connector part in said bore, and being moved to a second possession, free of said male connector part, by longitudinal displacement of said longitudinally displaceable element in said bore in a second longitudinal direction opposite to said first longitudinal direction, forcing said at least one tongue against said pivot element.

2. An electrical connector arrangement as claimed in claim 1 wherein said female connector part comprises a hollow cylindrical element having an end wall with a central opening therein communicating with said bore.

3. An electrical connector arrangement as claimed in claim 2 wherein said pivot element is disposed at said end wall adjacent said opening.

4. An electrical connector arrangement as claimed in claim 3 wherein said pivot element comprises a flange surrounding said opening.

5. An electrical connector arrangement as claimed in claim 3 wherein said pivot element comprises, for each tongue, a stud disposed at said end wall adjacent said opening.

6. An electrical connector arrangement as claimed in claim 1 wherein said locking plate comprises a washer having a plurality of tongues projecting into said opening and defining a spacing in said opening that is smaller than a diameter of said male connector part.

7. An electrical connector arrangement as claimed in claim 6 comprising two tongues disposed opposite each other in said opening.

8. An electrical connector arrangement as claimed in claim 6 comprising at least three tongues symmetrically projecting into said opening.

9. An electrical connector arrangement as claimed in claim 1 wherein said longitudinally displaceable element comprises a plunger having a central plunger bore therein adapted to receive said male connector part, said plunger being slidable in said bore of said female connector part.

10. An electrical connector arrangement as claimed in claim 9 wherein said central plunger bore has a peripheral edge mechanically acting on a peripheral portion of said at least one tongue to force said at least one tongue against said pivot element.

* * * * *